United States Patent [19]

Tovey et al.

[11] Patent Number: 5,647,372

[45] Date of Patent: *Jul. 15, 1997

[54] SPECIMEN RETRIEVAL POUCH AND METHOD FOR USE

[75] Inventors: H. Jonathan Tovey, Milford; Vinod Nagori, Danbury; Marina Korishch, Stamford, all of Conn.

[73] Assignee: United States Surgical Corporation, Norwalk, Conn.

[*] Notice: The portion of the term of this patent subsequent to Oct. 7, 2013, has been disclaimed.

[21] Appl. No.: 307,551

[22] Filed: Sep. 16, 1994

Related U.S. Application Data

[63] Continuation of Ser. No. 906,794, Jun. 30, 1992, abandoned.

[51] Int. Cl.$^6$ ............................................. A61B 10/00
[52] U.S. Cl. .................................. 128/749; 128/DIG. 24; 600/37
[58] Field of Search ............................ 604/22, 27, 28; 600/37; 606/110, 113, 114, 127; 128/749, 849–851, DIG. 24

[56] References Cited

U.S. PATENT DOCUMENTS

| | | |
|---|---|---|
| 30,471 | 10/1860 | Dudley . |
| 156,477 | 11/1874 | Bradford . |
| 1,609,014 | 11/1926 | Dowd . |
| 3,800,781 | 4/1974 | Zalucki . |
| 4,557,255 | 12/1985 | Goodman . |
| 4,744,363 | 5/1988 | Hasson . |
| 4,790,812 | 12/1988 | Hawkins, Jr. et al. . |
| 4,927,427 | 5/1990 | Kriauciunas et al. . |
| 4,997,435 | 3/1991 | Demeter . |
| 5,037,379 | 8/1991 | Clayman et al. . |
| 5,074,867 | 12/1991 | Wilk . |
| 5,084,054 | 1/1992 | Bencini et al. ........................ 606/113 |
| 5,143,082 | 9/1992 | Kindberg et al. . |
| 5,147,371 | 9/1992 | Washington et al. . |
| 5,176,687 | 1/1993 | Hasson et al. . |
| 5,190,542 | 3/1993 | Nakao et al. . |
| 5,190,555 | 3/1993 | Wetter et al. . |
| 5,201,740 | 4/1993 | Nakao et al. ........................ 604/45 X |
| 5,215,521 | 6/1993 | Cochran et al. . |
| 5,234,439 | 8/1993 | Wilk et al. . |
| 5,279,539 | 1/1994 | Bohan et al. ........................ 600/37 |
| 5,312,416 | 5/1994 | Spaeth et al. ........................ 606/114 |
| 5,352,184 | 10/1994 | Goldberg et al. ........................ 606/114 |
| 5,354,303 | 10/1994 | Spaeth et al. ........................ 604/27 |
| 5,465,731 | 11/1995 | Bell et al. ........................ 600/37 |
| 5,486,183 | 1/1996 | Middleman et al. ........................ 606/127 |

OTHER PUBLICATIONS

"Operative Pelviscopy–Endoscopical Ligatures Using the Loop–Ligation–Endo–Loop." by K. Semm, Kiel/W. Germany.
Davol Rubber Company Catalogue, p. 24, 1959.
Gallbladder Extraction™ page from publication describing Endopouch retrieval bag.
"Introducing the Pleatman Sac" advertisement from *Surgical Laparoscopy & Endoscopy*, vol. 2, No. 1, Mar. 1992.
Endopouch™ Brochure, Ethicon.
Endobag™ Brochure, Dexide.
Laparobag™ Advertisement, Endomedical Specialties.
Kent III RB et al., *Hemostasis of the Gallbladder Fossa During Laparoscopic Cholecystectomy*; Surg Laparoscopy & Endoscopy 1991; 1(2):104–105.
Kent III RB et al., *Laparoscopic Retrieval of Spilled Stones*; Surg Laparoscopy & Endoscopy 1992; 2(2):152–153.

*Primary Examiner*—John G. Weiss
*Assistant Examiner*—Dennis Ruhl

[57] ABSTRACT

A specimen removal pouch and applicator includes a pouch fabricated from a flexible membrane, a drawstring thread forming a running noose disposed circumferentially round the end of the pouch, an endoscopic tubular portion, and a pusher rod having an aperture for permitting the passage therethrough of a single thread. When the drawstring thread is pulled, the knot is stopped at the aperture and the noose is closed, thereby closing the mouth of the pouch. The pouch is detached from the apparatus.

69 Claims, 14 Drawing Sheets

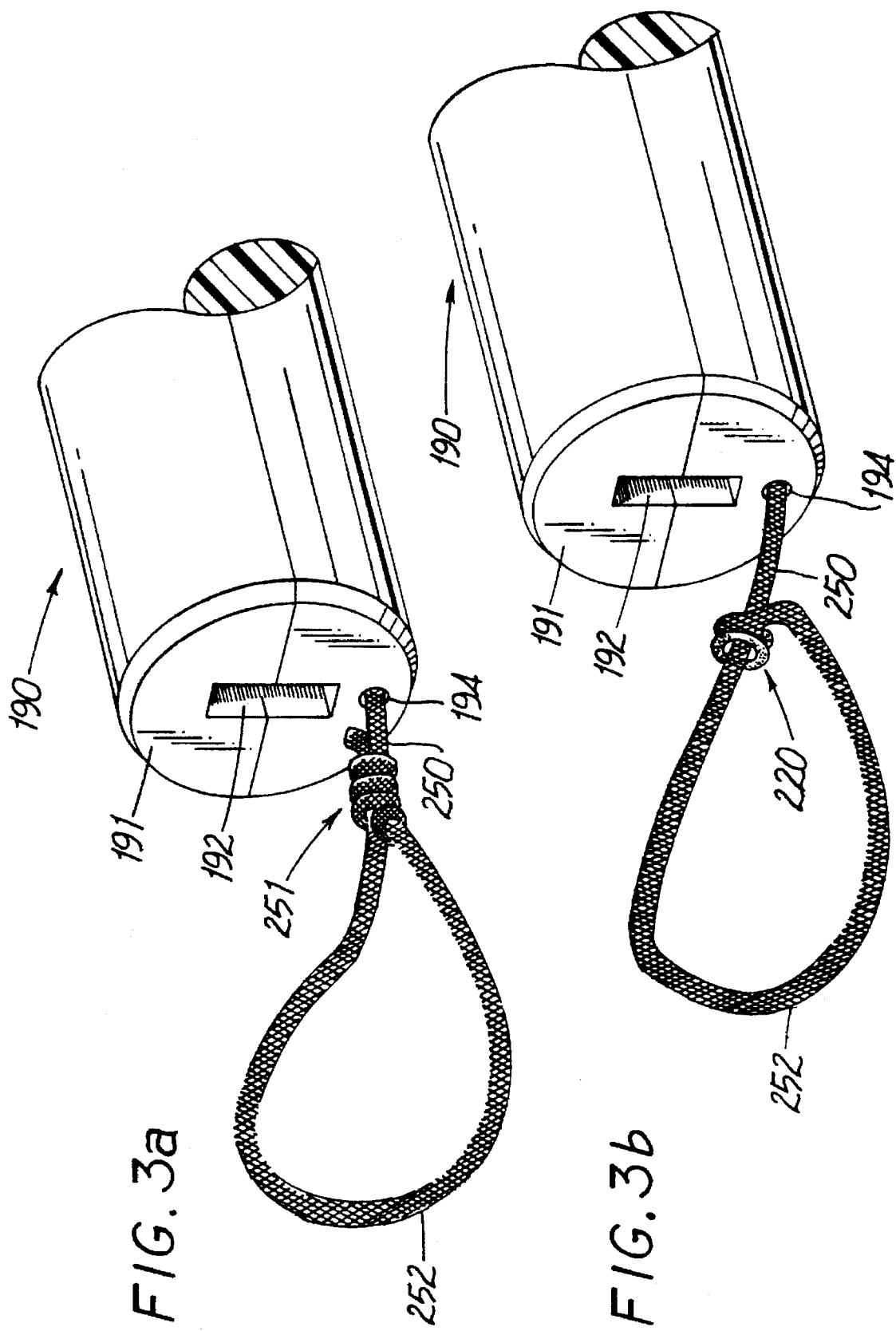

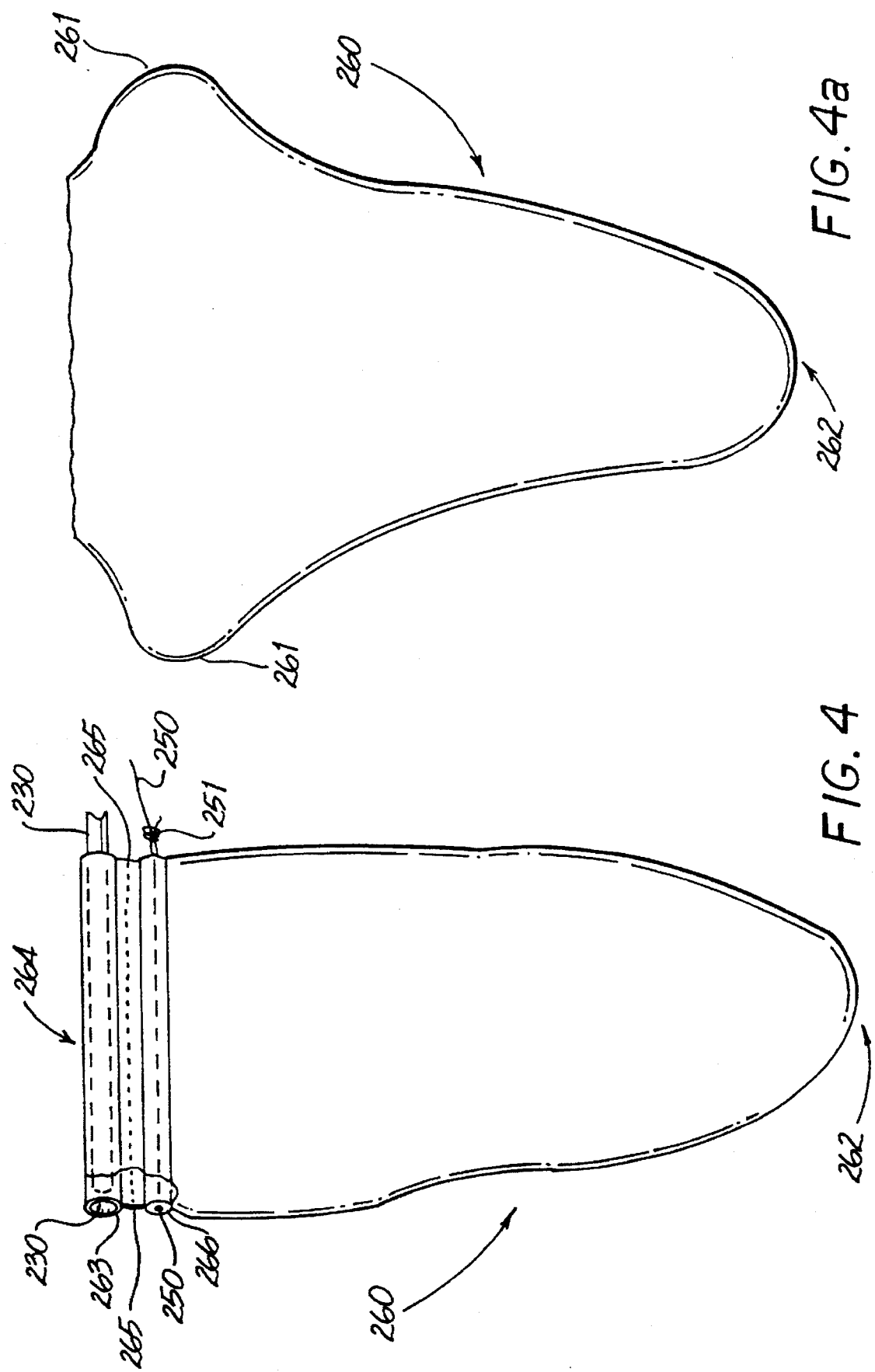

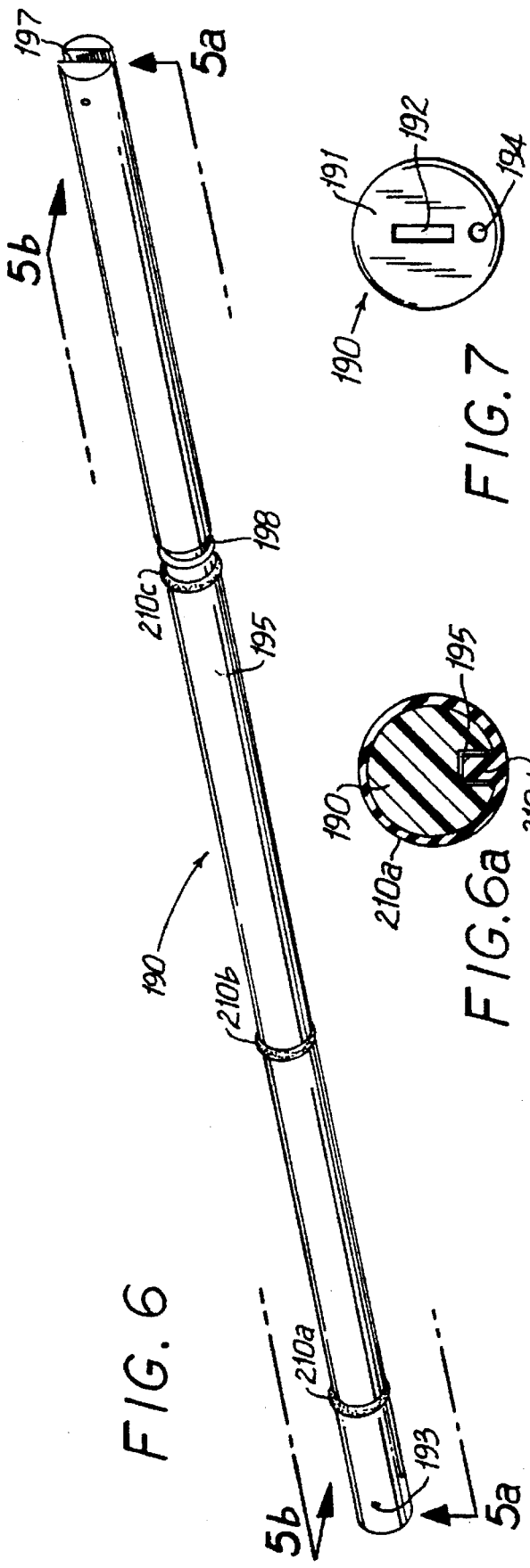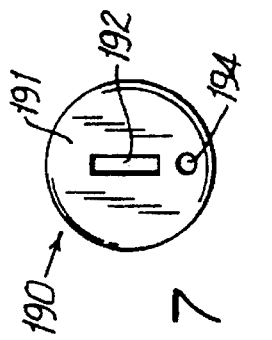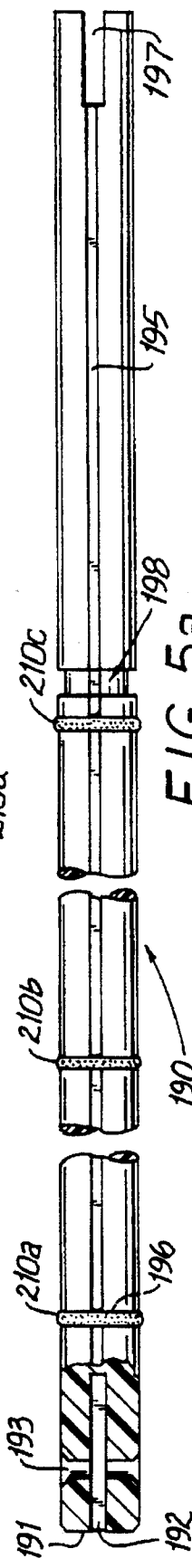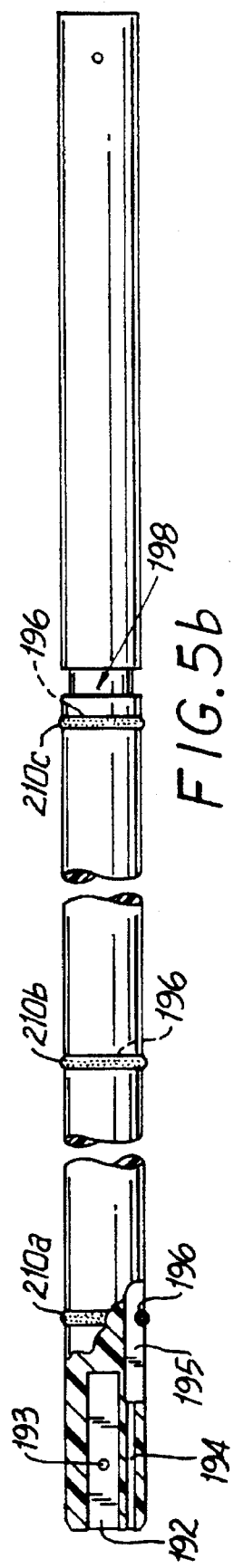

SPECIMEN RETRIEVAL POUCH AND METHOD FOR USE

CROSS REFERENCE TO RELATED APPLICATIONS

This is a continuation application of U.S. application Ser. No. 07/906,794 filed Jun. 30, 1992, now abandoned.

BACKGROUND OF THE INVENTION

1. Field of the Invention

The present invention relates to a surgical containment apparatus and method for use. More particularly, the present invention relates to a specimen retrieval pouch and method for its use in minimally invasive surgical procedures.

2. Background of the Art

Laparoscopic and endoscopic surgical procedures are minimally invasive procedures in which operations are carded out within the body by means of elongated instruments inserted through small entrance openings in the body. The initial opening in the body tissue to allow passage of the endoscopic or laparoscopic instruments to the interior of the body may be a natural passageway of the body, or it can be created by a tissue piercing instrument such as a trocar. Laparoscopic and endoscopic procedures generally require that any instrumentation inserted in the body be sealed, i.e. provisions must be made to ensure that gases do not enter or exit the body through the instrument or the entrance incision so that the surgical region of the body, e.g. the peritoneum, may be insufflated. Mechanical actuation of such instruments is for the most part constrained to the movement of the various components along a longitudinal axis with means provided to convert longitudinal movement to lateral movement where necessary. Because the endoscopic or laparoscopic tubes, instrumentation, and any required punctures or incisions are relatively narrow, endoscopic or laparoscopic surgery is less invasive and causes much less trauma to the patient as compared to procedures in which the surgeon is required to cut open large areas of body tissue.

Minimally invasive procedures are often used to partially or totally remove body tissue or organs from the interior of the body, e.g. nephrectomy, cholecystectomy and other such procedures. During such procedures, it is common that a cyst, tumor or other affected tissue or organ must be removed via the access opening in the skin, or through a cannula. Various types of entrapment devices have been disclosed to facilitate this procedure.

For example, U.S. Pat. No. 5,037,379 to Clayman et al. discloses a surgical tissue bag for percutaneously debulking tissue by morcellation. The bag includes a layer of puncture-resistant material, a layer of moisture-resistant material and a drawstring. In a disclosed method of use, the bag is placed within the body cavity, the body tissue or organ is placed within the bag, the opening of the bag is pulled through the incision in the skin leaving the distal end of the bag containing the tissue or organ within the body cavity, a morcellator is then inserted into the bag, and then the tissue or organ is alebulked and suctioned out of the bag.

U.S. Pat. No. 5,074,867 to Wilk discloses a planar membrane having filaments attached to its corners. The membrane is placed within a body cavity with the filaments extending through the trocar cannula to the outside of the body. The organ or tissue to be removed is placed on the membrane and the filaments are pulled to close the membrane around the organ and draw it through the cannula, if the organ is sufficiently deformable. If the organ is not sufficiently deformable, e.g. because of the presence of gall stones, a forceps or other instrument is used to crush the stones or tissue.

Although entrapment bags such as those described above are known, there remains a need for an improved specimen retrieval pouch to facilitate tissue removal in minimally invasive surgical procedures.

SUMMARY OF THE INVENTION

Provided herein is an apparatus for removing body tissue from the interior of the body in a minimally invasive surgical procedure. The apparatus includes a pouch having an openable end. The pouch is preferably part of a pouch assembly comprising the pouch and a pouch support. The pouch support can be attached to the drive means. The pouch may have perforations to facilitate detachment of the pouch from the support. The detachment can be simultaneous with the closing of the pouch in response to pulling the drawstring thread.

The apparatus may further include a drawstring thread forming a running noose disposed circumferentially around the pouch in proximity to the openable end thereof; attachment means for slidably attaching a first end portion of the drawstring thread to a second end portion of the drawstring thread to from the running noose; an endoscopic tubular portion having a distal end for insertion into a body; drive means for moving the pouch (i.e., pushing or pulling the pouch) through the endoscopic tubular portion; and stop means having an aperture for permitting passage therethrough of a single thread, the second end portion of the drawstring thread extending through the aperture, and the aperture means possessing a surface for abutting and holding the attachment means.

The pouch can be fabricated from a material selected from the group consisting of polyurethane and latex and preferably is transparent. A running knot is the preferred attachment means.

Stop means is provided by a distal surface of the pusher means. The pusher means can be an elongated rod slidably disposed within the tubular portion. In the embodiment described below having only a single drawstring thread the aperture of the stop means has a diameter of large enough dimension to permit passage therethrough of only a single threadline, but smaller dimension than the attachment means. The aperture can be oriented parallel to the longitudinal axis of the pusher rod or transverse to the longitudinal axis of the pusher rod.

The apparatus can further include means for resiliently opening the openable end of the pouch, such as spring means circumferentially attached to the openable end of the pouch and movable between an elongated and narrow closed configuration and a rounded open configuration, the spring means being resiliently biased to the open configuration. The spring means, which can support the pouch as well as open it, is attached to the distal end of the drive means and is slidably movable through the tubular portion when in the closed configuration, and resiliently moveable to its open configuration when moved outside said tubular portion. The spring means can include two elastic prongs each having a proximal end portion having a side surface in facing relation to the side surface of the proximal end portion of the other elastic prong and fastened thereto, and each elastic prong further having a distal end portion joined to the distal end portion of the other prong by a flexible membrane, such as shrink-wrap type tubing, attached to both said end portions.

The pouch can have perforations extending circumferentially therearound between the locations of the spring means and the drawstring thread.

The apparatus preferably further includes at least one gaseous sealing means, such as a coating of viscous sealing material applied to the outer surfaces of the pusher means and the drawstring thread.

Knife means may be provided to cut the drawstring thread.

In use, the apparatus is inserted through a cannula which has been inserted into a body. The pouch is deployed by advancing the drive means. The body tissue is severed, if necessary and placed within the pouch. The pouch is then closed and detached from the apparatus. The neck of the pouch can then be brought to the distal end of the trocar and the whole assembly removed. Alternatively, the pouch containing the specimen of body tissue may be "parked" by permitting it to remain in the body cavity until a later time during the operation whereupon the pouch may be removed in conjunction with the same cannula, an alternative cannula, or through an opening in the wall of body tissue. Also contemplated is the debulking of the body tissue specimen by, for example, morcellation or cutting, in order to facilitate its removal through a cannula.

BRIEF DESCRIPTION OF THE DRAWINGS

Preferred embodiments of the invention are described hereinbelow with reference to the drawings wherein:

FIGS. 3a and 3b illustrate, respectively, in perspective view a running knot, and, as an alternative, an eyelet means for slidably attaching a first end portion of the drawstring thread to a second end portion for form a running noose.

FIG. 4 is an elevational partially cut away view of the specimen removal pouch assembly;

FIG. 4a is an elevational view of an alternative pouch having a circumferential flared section;

FIGS. 5a, 5b, 6 and 7 are, respectively, plan, elevational, perspective, and end views of the pusher bar;

FIG. 6a illustrates a side view of O-ring 210a;

DETAILED DESCRIPTION OF PREFERRED EMBODIMENT(S)

Figures 1A, 1B:
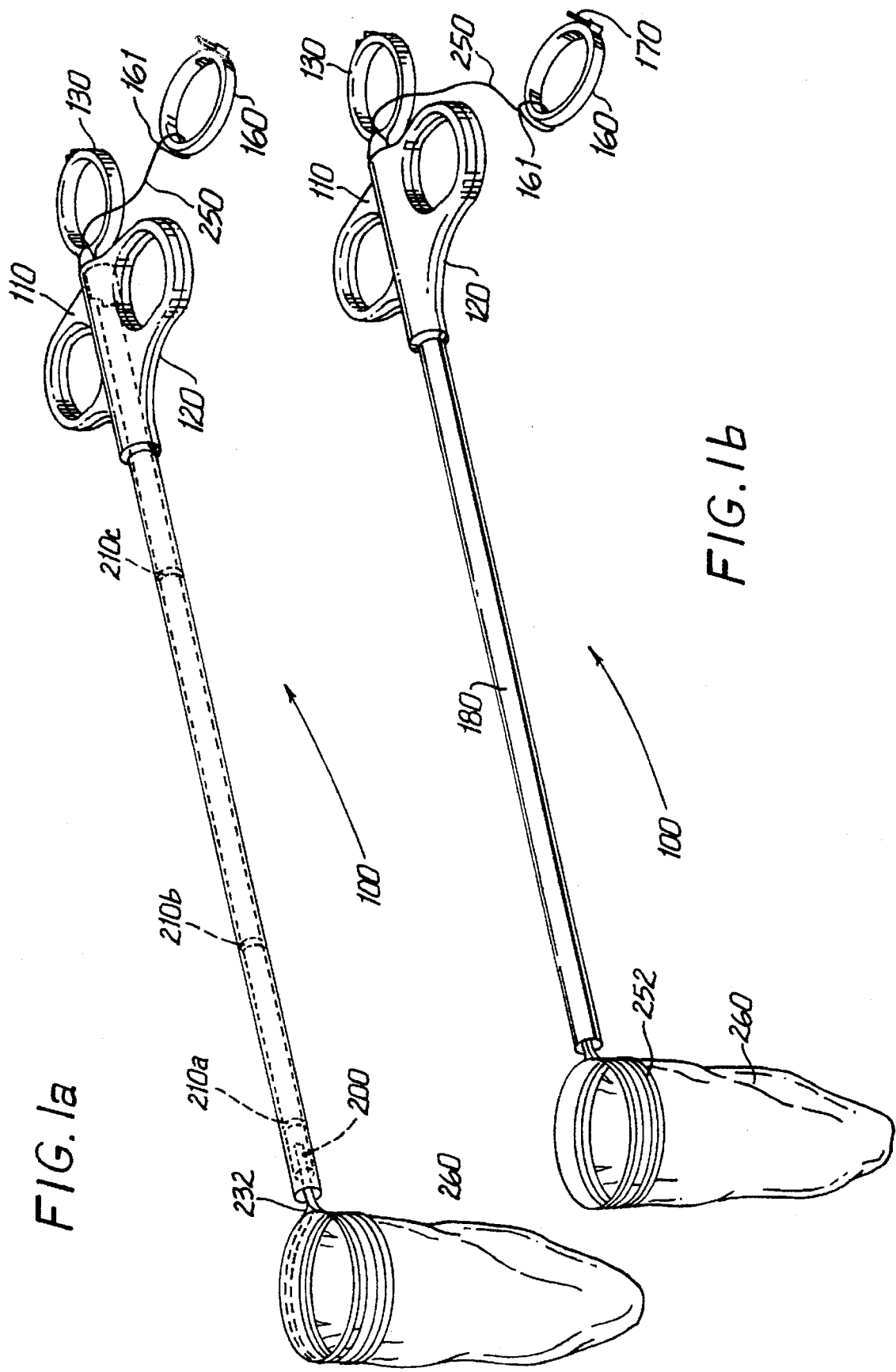
FIGS. 1a and 1b are perspective views of the apparatus of the present invention in the deployed configuration.

As used herein with reference to the present invention, the terms "laparoscopic" and "endoscopic" are interchangeable and refer to instruments having a relatively narrow operating portion for insertion into a cannula or a small incision in the skin, or to a surgical procedure in which such instruments are employed. Use herein of the term "laparoscopic" should not be construed so as to exclude "endoscopic" and use herein of the term "endoscopic" should not be construed so as to exclude "laparoscopic". To the contrary, it is believed that the present invention may find use in any procedure where access to the interior of the body is limited to a relatively small incision, with or without the use of a cannula, including, but not limited to, laparoscopic procedures.

APPARATUS

A preferred embodiment of the removal pouch and applicator assembly 100 of the present invention is shown in FIGS. 1 to 9.

Referring specifically to FIG. 4, the removal pouch 260 includes a flexible film or sheet preferably formed from a substantially transparent polymeric material. A preferred material is polyurethane sheet of about 0.001 to about 0.005 inches in thickness, although other biocompatible materials capable of forming a flexible membrane, such as, for example, latex, may be used, and other appropriate thicknesses. Preferably, the material is transparent to permit viewing of its contents. Also, the pouch material should be impervious to penetration by cancer cells.

The pouch may be of any dimensions suitable for the purpose of organ entrapment or removal. In the present embodiment, the pouch 260 has a diameter of from about 1.5 inches to about 3.0 inches and a depth of from about 2 inches to about 8 inches. The pouch 260 may be dimensioned and fabricated of a suitable material to allow treatment, e.g. morcellation or division, of the organ tissue, for example to reduce its bulk to facilitate withdrawal from the body cavity.

Pouch 260 includes a closed distal end portion 262 and an openable and closable end portion or mouth 264. Optionally, as illustrated in FIG. 4a, the pouch may include a circumferential wider diameter flared portion 261 in the vicinity of the open proximal end portion or mouth 264. The open proximal end portion or mouth 264 is defined by a proximal (upper) circumferential tubular portion or sleeve 263, and a distal (lower) circumferential tubular portion or sleeve 266, which are spaced apart from each other.

The pouch possesses a linear portion weakened by perforation or, more preferably, scoring, which extends circumferentially around the mouth 264 of the pouch between the proximal and distal sleeves 263 and 266, respectively. The scored line 265 may be created by induction heating to create a linear potion having thickness less than that of the original material to facilitate tearing of the material along the scored line 265.

The proximal sleeve 263 is adapted to receive a spring member 230, described below. The distal sleeve 266 is adapted to receive a drawstring 250. The scored portion 265 is adapted to tear when the drawstring 250 is pulled with sufficient force so as to close the mouth 264 of the bag distal to the perforation 265, thereby providing fast detachment of pouch 260 from the spring member 230 simultaneously with closure of mouth 264. Clearly, alternative means also can be utilized to detach the pouch 260 from the spring member 230, such as by pulling with a grasper or by cutting with a scissors.

Referring now to FIGS. 1a, 1b, 2 and 3, the laparoscopic removal pouch and applicator assembly includes an elongated tube 180 which is of such dimensions so as to be insertable through a trocar cannula for endoscopic or laparoscopic procedures.

Figure 2:
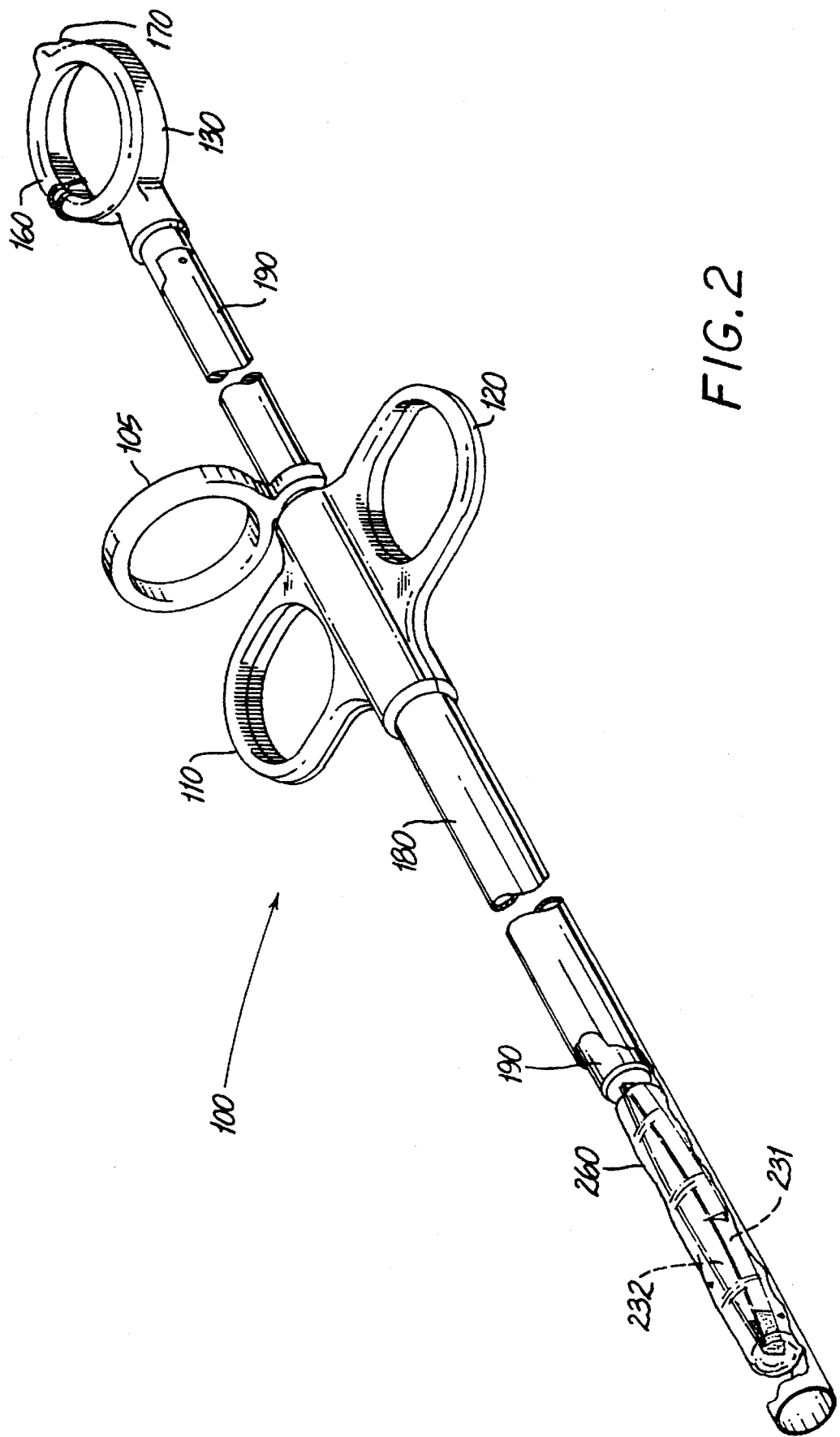
FIG. 2 is a perspective view of the apparatus in the initial, undeployed configuration.
Figure 16:
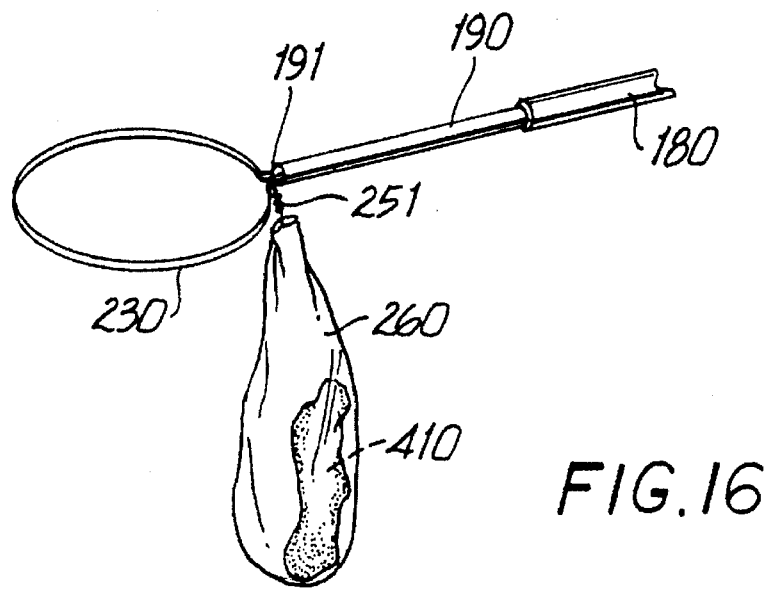

Referring additionally now to FIGS. 5, 6 and 7, the drive rod or bar is an elongated generally cylindrical member slidably disposed through the bore of tube 180. Pusher rod 190 includes a distal pushing end 191 and is attached to the pouch assembly to move the pouch from a non-deployed position contained within the outer tube 180 (as shown in FIG. 2) to a deployed position distal to the outer tube 180, (as shown in FIGS. 1a and 16. A spring retainer slot 192 extends longitudinally through the pusher rod and opens at the distal end 191. Aperture 193 extends transverse to the drive rod 190 across the spring retainer slot 192. Pin 200 is disposed through aperture 193 and through apertures 231b and 232b (See FIGS. 3, 5a and 5b) for fastening spring 230 within retainer slot 192.

Drawstring aperture 194 extends longitudinally through the drive rod opening distally at end 192. Drawstring aperture 194 opens proximally into drawstring slot 195, which extends longitudinally along the drive rod 190. Drawstring slot 195 terminates at its proximal end at slot 197. Proximal slot 197 is adapted to receive finger loop 130. Drive rod 190 also includes circumferential slots 196 for receiving O-rings 210a, 210b and 210c. The O-rings help maintain a gaseous seal and/or help to maintain the drawstring in place while permitting sliding movement of the drive bar 190 through tube 180. As shown in FIG. 6a, O-ring 210a includes an inwardly pointing projection 210d for providing additional fluid sealability.

The drive bar 190 is preferably fabricated from a strong polymeric material. A material suitable for fabricating the drive rod 190 is polycarbonate plastic with 20% glass fiber filler. Other materials suitable for the purposes discussed herein may also be used. To maintain a gaseous seal within the instrument, close tolerances are observed. The outer diameter of the drive rod 190 is slightly less than the inner diameter of the tube 180 through which it slides longitudinally. Additionally, the drive rod 190 is preferably coated with a silicone grease as a viscous sealing material to insure that no gases exit or enter the body through the seal when the operation site (e.g. the peritoneum or other body cavity) is insufflated. A locking tab 105 is included to prevent premature actuation of the instrument during shipping. The locking tab includes snap fit engagement means to engage slot 198 of the drive bar. When thus engaged, the drive bar cannot be pushed distally beyond the point where the locking tab 105 engages the proximal end of the handle portions 110, 120. To actuate the instrument the surgeon must first disengage the locking tab by pulling it off the instrument.

The spring 230 comprises two flexible and resilient strips 231 and 232 which, in unstressed or freely expanded condition together form a generally circular hoop for supporting the periphery of opening 264 of pouch 260. Each strip 231 and 232 has a proximal end portion, 231a and 232a, respectively, with apertures 231b and 232b extending laterally therethrough. The proximal end portions 231a and 232a are adapted to be received into slot 192 of the drive rod 190 so that longitudinal movement of the pusher rod 190 in the manner described below will move spring 230 and attached pouch 260. Apertures 231b and 232b are configured so as to align with aperture 193 of the pusher bar, thereby permitting disposition therethrough of pin 200. The distal ends 231c and 232c, respectively, meet in opposing relationship where they are joined by tubing 240 made from polymeric, and preferably shrink-wrap type material. Spring 230 is preferably fabricated from a super elastic metal. One example of such super elastic metal is TINEL brand metal available from Raychem Corporation of Menlo Park, Calif. Other resilient materials are also contemplated, including plastic or stainless steel.

Figure 3:
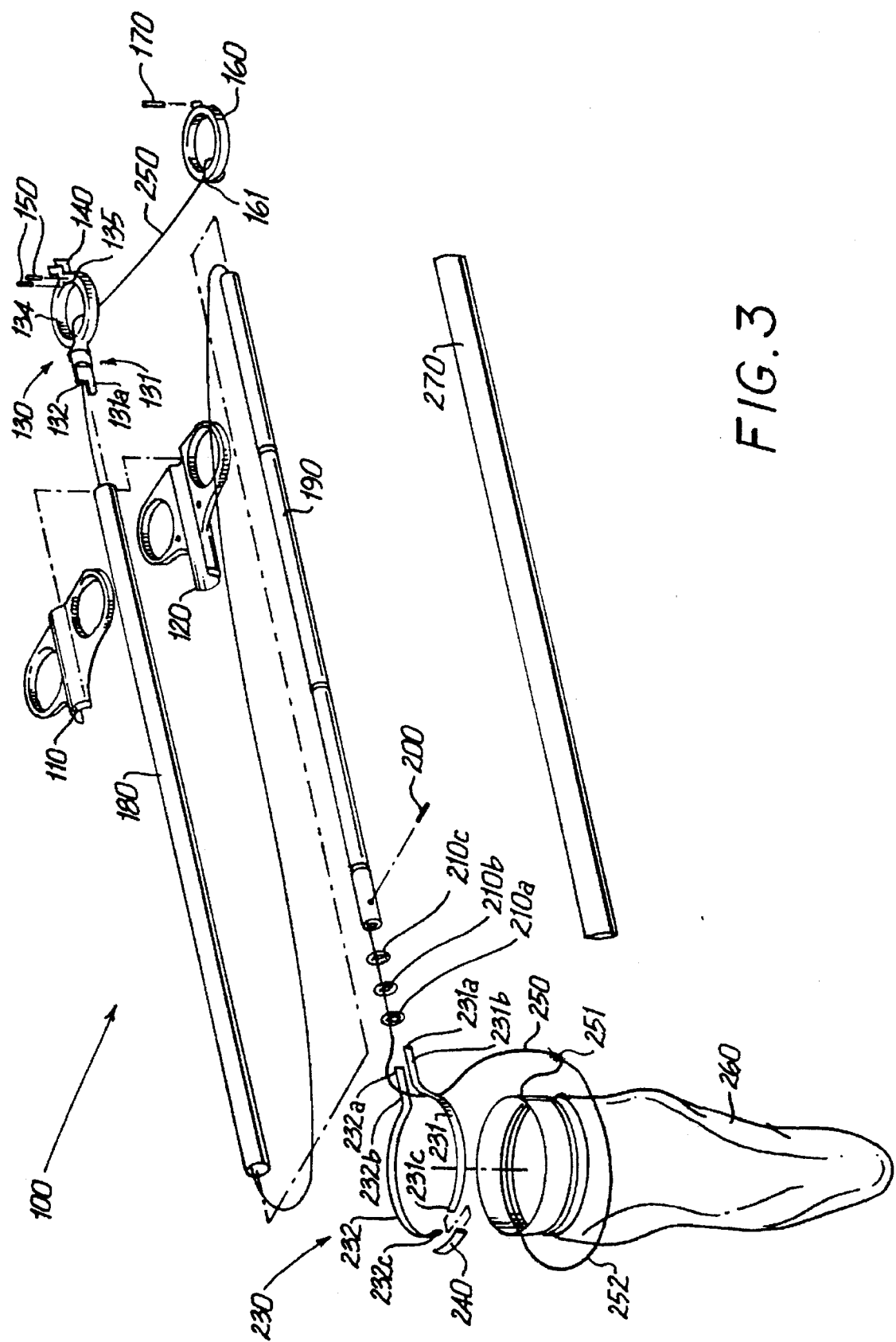
FIG. 3 is an exploded perspective view of the apparatus.
Figure 9:
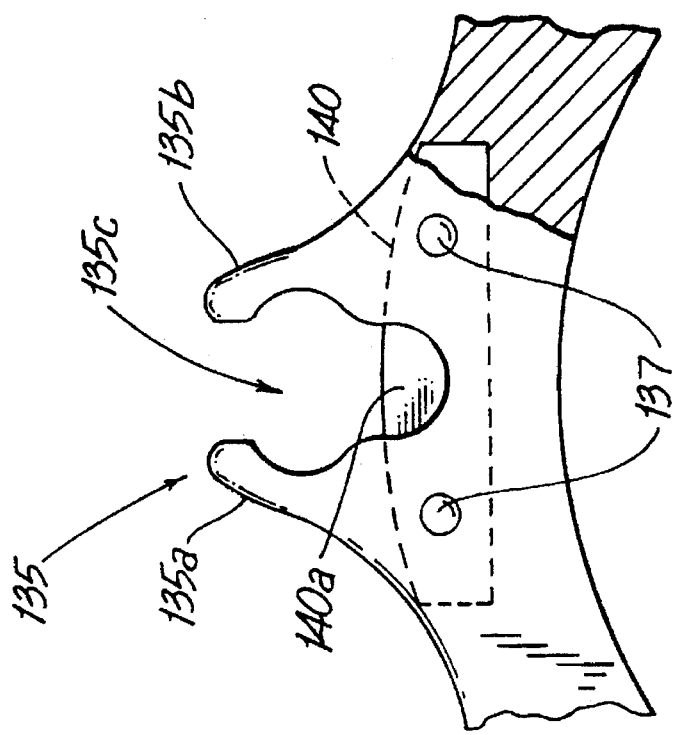
FIG. 9 is a detached view of the fixture at the proximal end of the finger loop.
Figure 8:
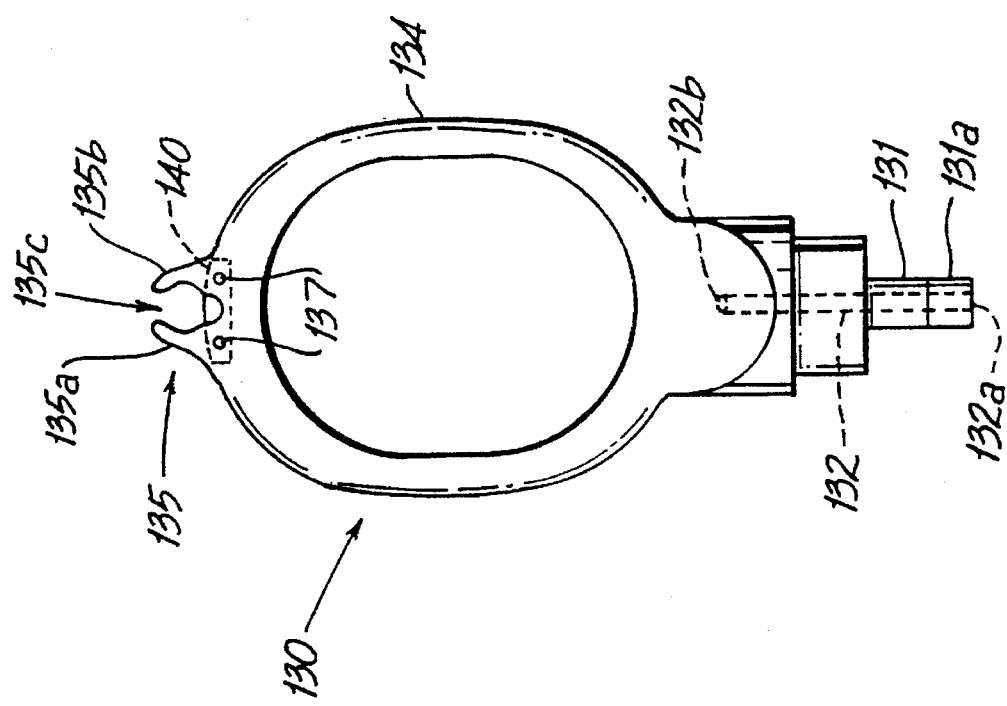
FIG. 8 is a bottom plan view of the finger loop.

Referring now to FIGS. 3, 8 and 9, the finger loop 130 includes a ring portion 134 for engagement by a user's finger. The distal end of the finger loop includes projection 131 for engaging slot 197 in the drive rod 190, wherein the projection 132 is fixedly attached. Projection 131 includes a key portion 131a which engages a corresponding notch in the handle portion 120 to prevent relative rotation of the drive rod within the apparatus when the pouch is fully deployed. Aperture 132 extends longitudinally from distal opening 132a to proximal opening 132b. Aperture 132 receives thread 250. At its proximal end, finger loop 130 possesses a fixture 135 for releasably holding pull ring 160. Fixture 135 comprises spaced apart generally proximally pointing prongs 135a and 135b which define a proximally opening mouth 135c for snap-fit reception of post 170 of the pull ring 160. Knife 140 is mounted laterally across the mouth at the distal end thereof with sharp knife edge 140a pointed proximally. The knife blade 140 is secured at the fixture 135 by means of pins 150 disposed through apertures 137 in the finger loop 130. The knife edge 140a functions to cut the drawstring 250, as will be described below. Alternatively, the knife can be insert molded onto the finger loop 130.

Referring to FIG. 3, handle portions 110 and 120 are fixedly joined together to form a unitary ring handle, which is fixedly mounted to the proximal end of tube 180 for receipt of a user's finger to facilitate manipulation of the instrument.

Pull ring 160 is a finger ring to facilitate pulling of drawstring 250 to which it is attached, preferably by means of an adhesive. Post 170, which may be in integral part of pull ring 160, is pivotally mounted into mouth 135c of fixture 135 in a snap-fit engagement and may be disengaged by exerting a pulling force thereon to separate ring 160 from ring portion 134 for reasons discussed below. The pull ring 160 preferably includes a projection 161 which is engageable with a corresponding depression in the finger ring 130 to prevent inadvertent or unintended pivoting of the pull ring 160. In a preferred embodiment, the pull ring is distinctively colored to alert the user as to the orientation of the pouch 260.

Drawstring 250 is tied at one end to pull ring 160, and extends through aperture 132 in the finger loop, through drawstring slot 195 in the pusher bar, through drawstring aperture 194, and around the mouth 264 of the pouch through lower tubular chamber 266. The drawstring is preferably coated with a silicone grease as a viscous sealing material to insure that gases do not enter or exit the peritoneum through aperture 194. The end of the drawstring is brought around and tied to the drawstring to form a noose 252 tied by knot 251. Knot 251 is a "running knot", i.e. a knot that slips along the rope or line around which it is tied. Thus, noose 252 tightens when the standing part of the line is pulled. For proper operation, knot 251 should have a size larger than the diameter of aperture 194. When drawstring 250 is pulled proximally, the knot 251 will be pulled up to the distal opening of aperture 194 where the knot 251 will abut the distal face 191 of pusher rod 190. Aperture 194 has a diameter large enough to admit a single threadline of drawstring 250 with minimal clearance to help maintain a gaseous seal with further sealing provided by the silicone grease, but not large enough to permit knot 251 to pass through. Thus, knot 251 is retained in position while drawstring 250 is pulled proximally, thereby closing noose 252.

This, in turn, closes mouth 264 of pouch 260 and detaches the lower portion of pouch 260 along perforation 265. Use of the running knot enables closure of the pouch to be achieved by a single actuating line of drawstring thread moving through the apparatus. An aperture or thread passage in a laparoscopic instrument for accommodating a single line of thread need not have as large a diameter as that for accommodating two or more lines of drawstring thread.

A further advantage is that it is easier to maintain a proper gaseous seal within aperture 194 when a single thread is moved therethrough than if two or more lines of thread were disposed therethrough. Although apparatus configurations having only a single actuating threadline are preferred, also contemplated as being within the scope of the present invention are apparatus employing multiple actuating threadlines from, for example, two or more threads, or doubled-over single threads.

Any type of running knot having the proper diameter may be used, such as the slip knot, running bowline, or, more preferred, the "hangman's noose" and variations thereof. The knot preferably should maintain enough friction on the drawstring such that the knot slides along the drawstring when the drawstring is pulled with sufficient tension, but not otherwise. The knot will, therefore, slide in only one direction.

The present invention contemplates means other than knots for accomplishing the same function as described above. For example, rings, eyelets, and the like may be used. As shown in FIG. 3A, one end of the drawstring thread is attached to ring member 220, which has an aperture 221 for receiving drawstring 250. When the drawstring 250 is pulled proximally, ring member 220 abuts the proximal face 181 at aperture 194, permitting drawstring 250 to be pulled through, thereby closing noose 252.

Thus, any means for slidably attaching one end of the drawstring to the drawstring thread to form a reducible loop, or running noose, is contemplated as being within the scope of the present invention.

Tube 180 is of such diameter as to permit it to be slidably disposed through a trocar cannula for use in endoscopic or laparoscopic operations, and is generally between about 0.25 inches to 0.50 inches in diameter, and about 10 inches to about 15 inches long, although other dimensions may also be used if appropriate to the operation being performed. Tube 180 slidably houses the pusher bar 190 and, when undeployed, the spring 230 and pouch 260. In the initial, unused condition, pouch 260 will be rolled up and spring portions 231 and 232 will be relatively straight and positioned within tube 180. When the pusher red 190 is advanced, the spring 230 connected thereto will exit the distal end of tube 180 and resiliently pop open, thereby deploying and opening pouch 260. Tube 180 is preferably from a metal such as stainless steel and is preferably coated with a shrink wrap plastic such as shrinkable polyethylene fiberglass, or polyvinyl chloride of a grade suitable for use in surgical procedures.

METHOD(S)

Introduction

Minimally invasive surgery in the abdomen usually requires the placement of one or more trocar assemblies in the abdominal wall to provide access to the peritoneum for the surgical instruments. The trocar assembly may include an obturator with a sharp, tissue piercing point, a cannula having a tube and a proximal section which usually includes valve and sealing means. The surgeon inserts the trocar assembly into the abdominal wall and then removes the obturator leaving the cannula inserted into the body cavity and the proximal section outside the body. The body cavity is then insufflated. Additional cannulas can be inserted and various operating and optical viewing instruments may be inserted through the several cannulas. The cannula sealing means helps prevent the entry or escape of gas between the inside of the cannula and the outside of the instrument. As mentioned before, the instruments generally have internal sealing means to prevent the escape or entry of gas through the interior of the instrument. Placement of trocar cannulas and insertion of instruments therethrough are performed in accordance with methods and apparatus known and commonly available to those with skill in the art.

Method of the Present Invention

Referring now to FIGS. 10 to 20, a method of using the apparatus of the present invention in minimally invasive surgery will now be described. By way of illustration, surgical procedures in which the method of the present invention may be used include, but are not limited to, nephrectomy, cholecystectomy, appendectomy, and the like.

Figure 10:
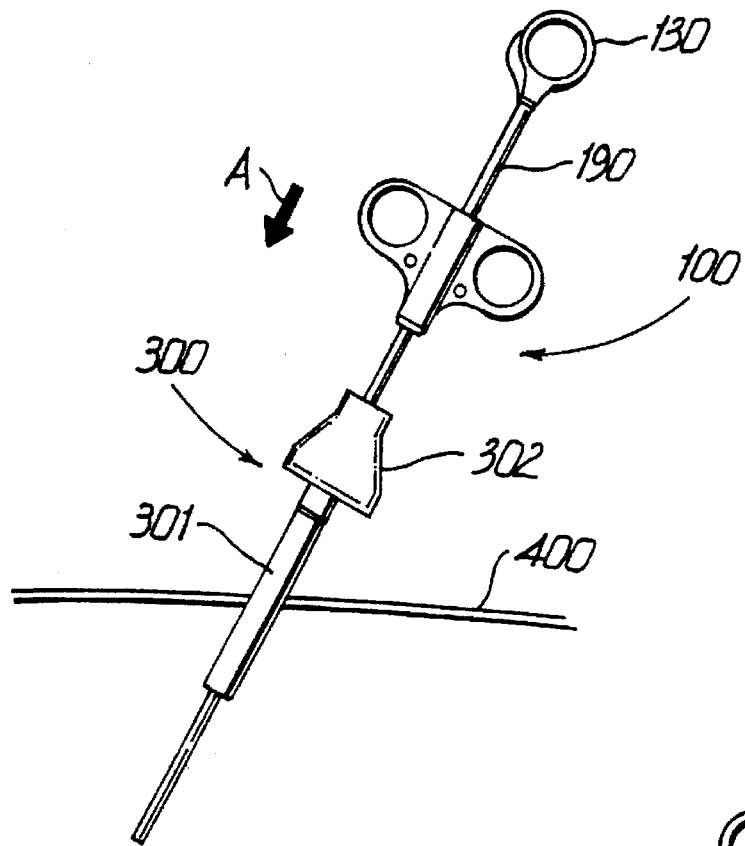
FIG. 10 illustrates the insertion of the apparatus of the present invention through a trocar cannula into a body cavity.

FIG. 10 shows a diagrammatic view of a trocar cannula 300 inserted through a wall of body tissue 400 to gain access to a body cavity, such as for example the peritoneum. The applicator assembly 100, with the specimen retrieval pouch in the non-deployed position is inserted through the cannula 300 in the direction of arrow A such that the distal end of the applicator assembly 100 is positioned within the body cavity. As depicted in FIG. 10, the applicator assembly is in the initial condition with specimen retrieval pouch 260 retained within tube 180. Pull ring 160 is positioned atop post 170. The locking tab 105 is removed at this time to permit actuation of the instrument.

Figure 11:
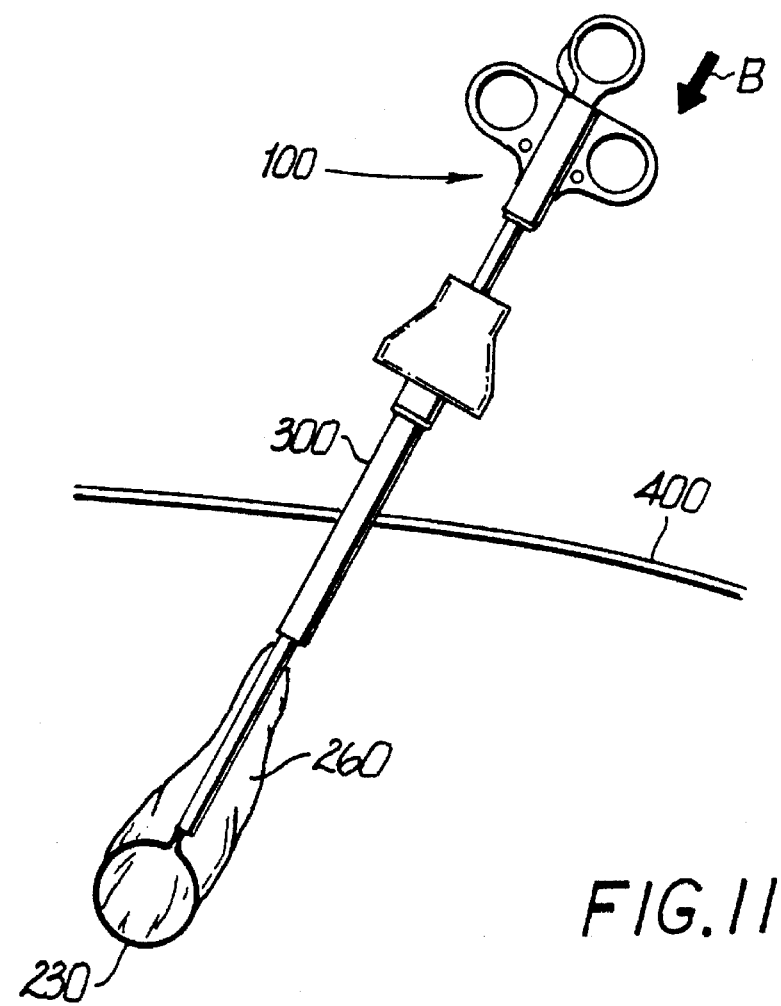
FIGS. 11 and 12 illustrate deployment of the specimen removal pouch.

Referring now to FIG. 11, the drive rod 190 is advanced longitudinally distally by the surgeon's pushing of the finger loop 130 as indicated by arrow B. The finger loops of ring portion 110 (and 120) may be grasped by the user during the movement of finger loop 130. This movement, of drive rod 190 advances the pouch 260 beyond the distal end of tube 180 where spring 230 is no longer restrained by tube 180 and, therefore, resiliently pops open to its substantially round configuration to thereby open the mouth 264 of the pouch.

Figure 12:
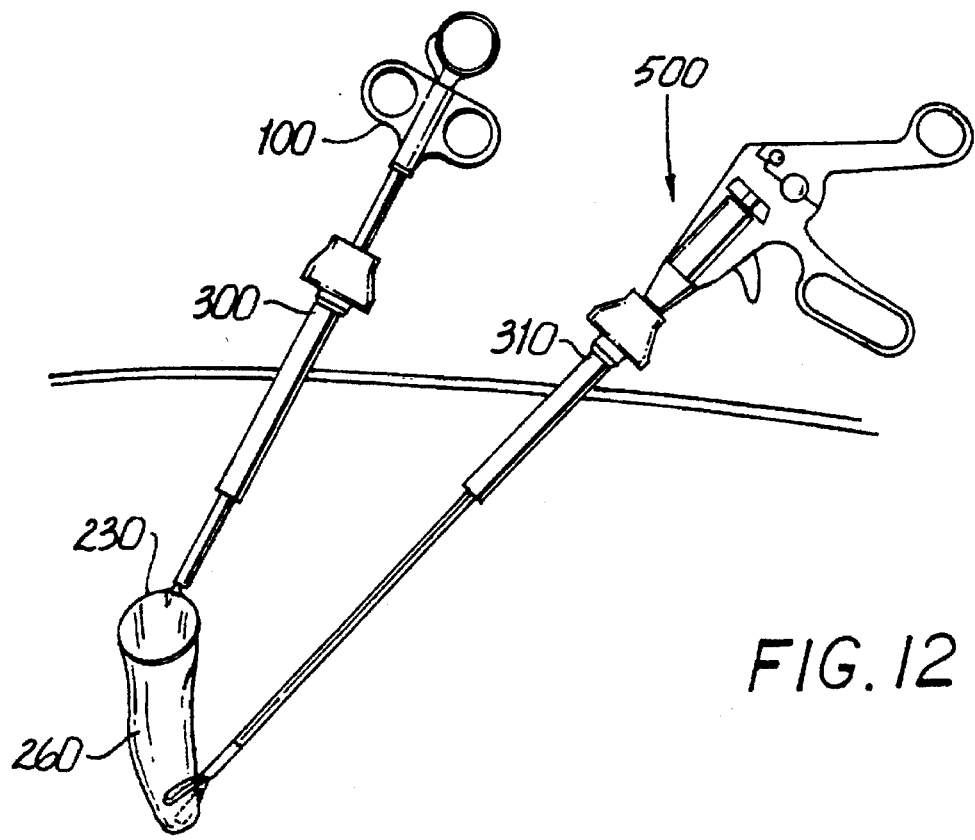

Referring now to FIG. 12, non-traumatic forceps or graspers 500 may be inserted through another cannula and manipulated to gently unroll the pouch 260 if necessary.

Figure 13:
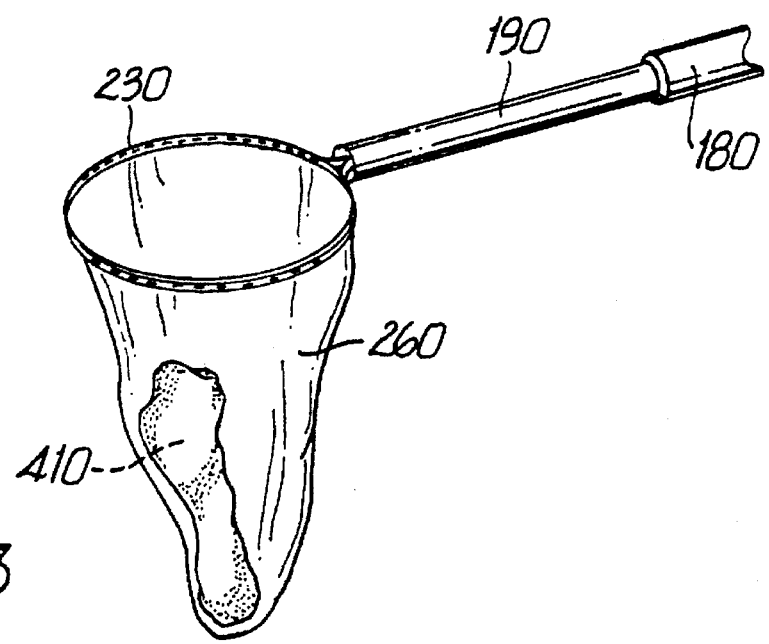
FIG. 13 illustrates the entrapment of a tissue specimen.

Referring to FIG. 13, the specimen of body tissue 410 is excised and placed into pouch 260. The specimen may optionally be treated, i.e. morcellated or otherwise divided prior to removal from the body cavity.

Figure 15:
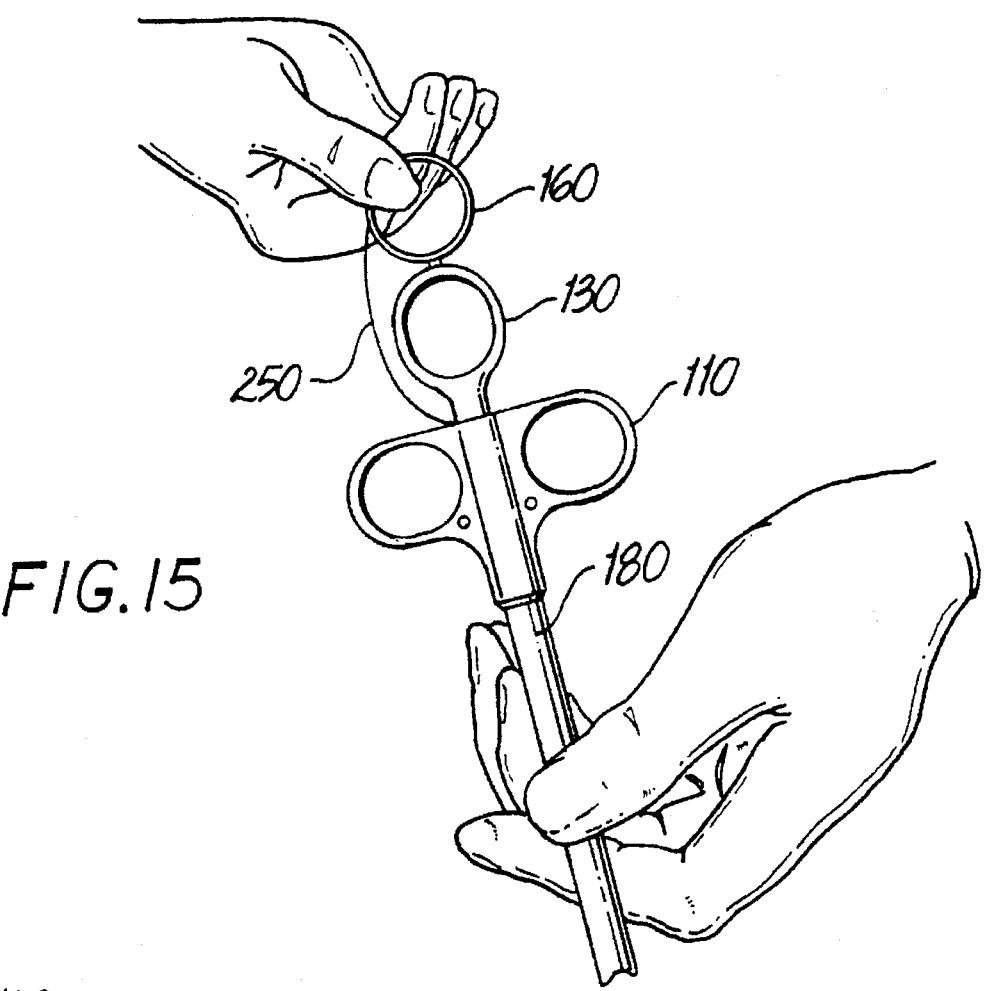
FIGS. 14, 15 and 16 illustrate closure of the pouch.
Figure 14:
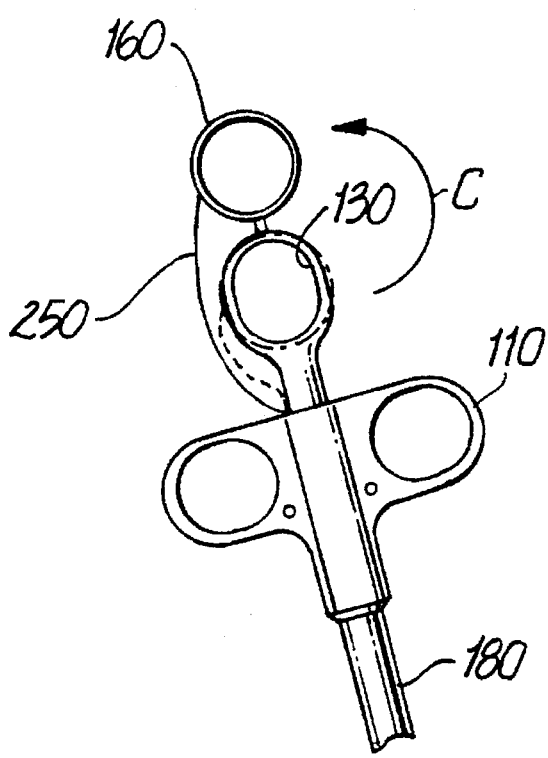

Referring to FIG. 14, the pull ring 160 is pivoted with post 170 in a direction as shown by arrow C to a position as illustrated in FIG. 15.

Referring to FIG. 15, the pull ring 160 is grasped and pulled thereby disengaging post 170 from fixture 135 and permitting removal of pull ring 160 from the finger loop 130.

When the pull ring 160 is pulled (FIG. 16), drawstring 250 is moved proximally, thereby detaching the pouch 260 from the spring support 230 along perforation line 265. Continued pulling of the drawstring 250 will bring running knot 251 into abutment with the distal end 191 of the pusher thus reducing noose or loop 252 and closing the mouth of the pouch 260.

Figure 17:
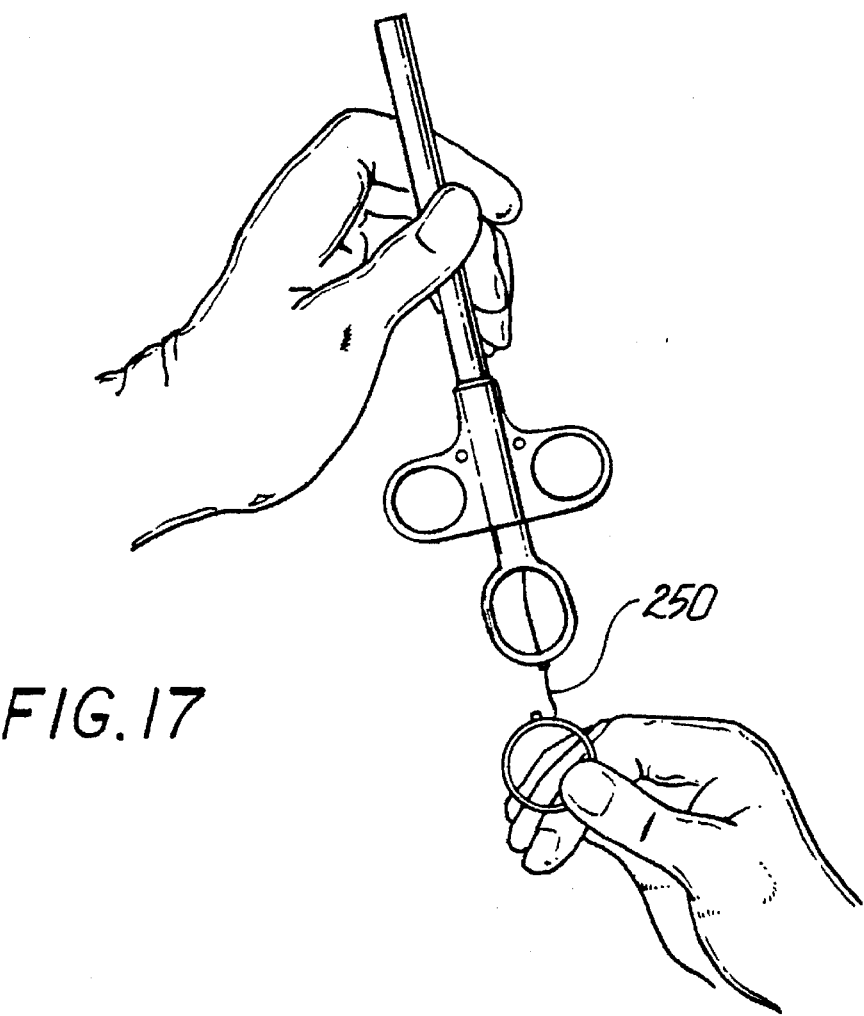
FIG. 17 illustrates cutting of the drawstring.

Referring to FIG. 17, the drawstring 250 is inserted into mouth 135c of fixture 135 and cut by knife 140 to allow for subsequent removal of the instrument with the closed pouch remaining inside the body cavity.

Figure 18:
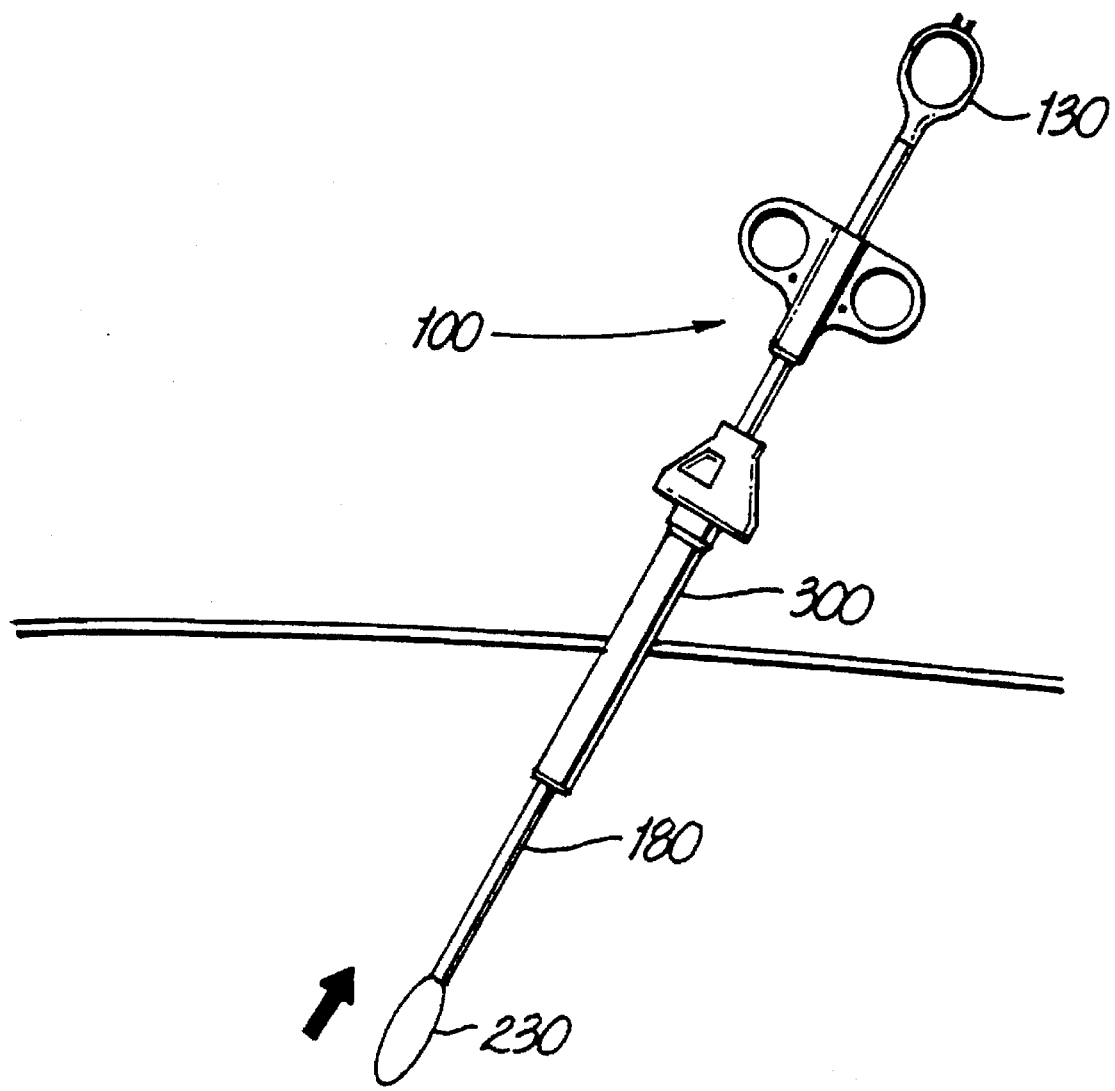
FIG. 18 illustrates removal of the apparatus from the cannula.

Referring to FIG. 18 the finger loop 130 is pulled so as to withdraw spring 230 back into tube 180, whereupon spring 230 refolds back into its pre-deployed relatively straight configuration to permit removal of the apparatus 100 from the cannula 300. The drive rod 190 is not retracted completely out of the proximal end of tube 180, since complete retraction of the drive rod will permit exit of the spring 230 and subsequent opening of the spring 230 outside the proximal end of the apparatus.

Figure 19:
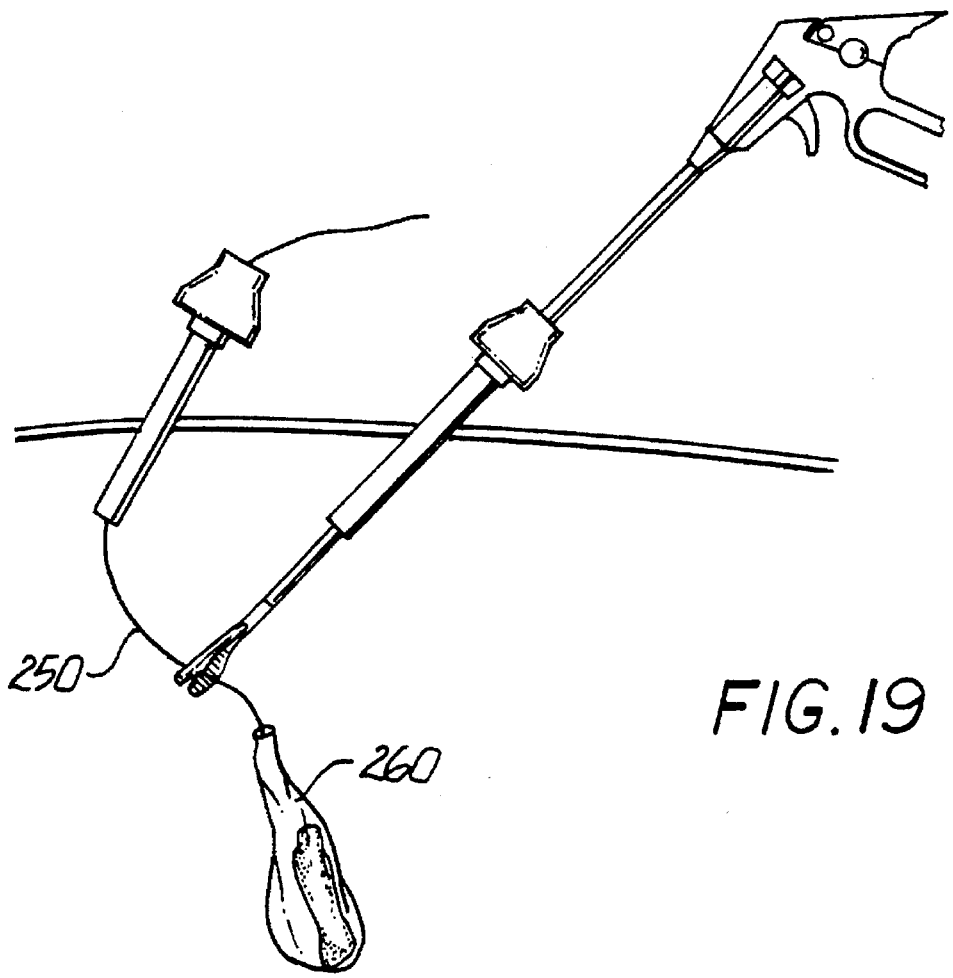
FIGS. 19 and 20 illustrate follow-up procedures for removal of the pouch.
Figure 20:
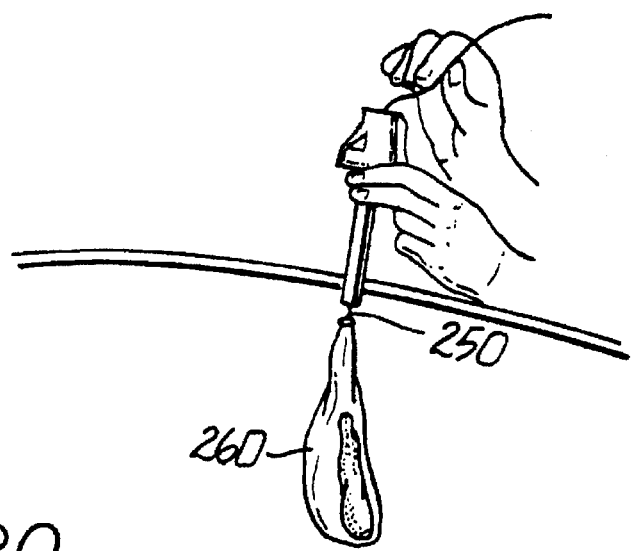

At this point drawstring 250 is sitting in the cannula and as shown in FIG. 20, the pouch with tissue specimen can be immediately removed through the trocar site by pulling the drawstring 250 through the cannula until the end of the pouch 260 reaches the neck of the trocar and both can be removed together, or the trocar can be removed first and removed thereafter through the same incision. Alternatively, with the drawstring securely holding the pouch closed, the drawstring may be grasped by an appropriate endoscopic instrument, such as a grasper, and held inside the body cavity, as shown in FIG. 19, and removed at a later time during the operation. If necessary, the incision may be enlarged to permit passage therethrough of the pouch and specimen. However, it is alternatively contemplated that if the specimens contained in the pouch is sufficiently small, or if divided as discussed above, it can be removed through the cannula.

ALTERNATIVE EMBODIMENT

Figure 21:
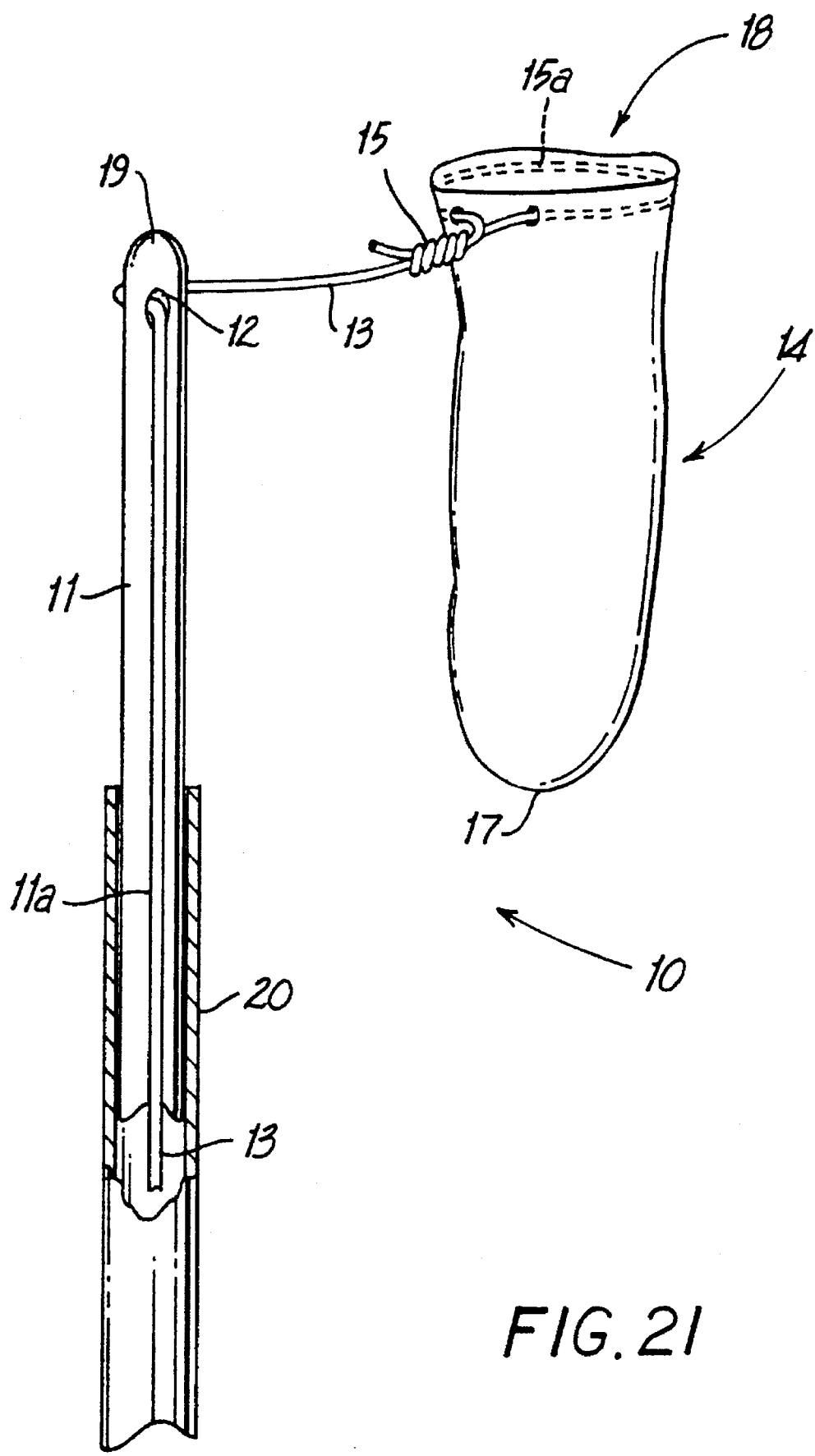
FIG. 21 illustrates an alternative embodiment in a partially cutaway view.

FIG. 21 illustrates an alternative embodiment of a laparoscopic removal pouch assembly 10. The flexible removal pouch 14 has a closed distal end 17 and an open proximal end 18. The pouch is preferably fabricated from a latex or other material suitable for use in surgical procedures. A drawstring 13 is disposed laterally through transverse aperture 12 in proximity to the distal end of the push rod 11. Push rod 11 is an elongated member having a blunt end 19 for pushing pouch 14 through a cannula 20. Preferably, push rod 11 has a longitudinal slot 11a through which the drawstring thread 13 may be disposed. The drawstring 13 is disposed around the open end 18 of the pouch 14 to form a loop in a sewn-in type construction 16, whereupon it terminates in a running knot 15 to form running noose 15a. The aperture 12 has a diameter large enough to admit drawstring 13, but not large enough to permit running knot 15 to pass through.

In use, the blunt end 19 of the push rod 11 is used to push the inner surface of closed end 17 to insert pouch 14 through a cannula inserted through an opening in a tissue wall into a body cavity. The pouch 14 is removed from the rod 11 by means of a grasper inserted through another cannula and positioned in proximity to the tissue severed for removal. The pouch 14 is manipulated so as to scoop up the tissue into the closed end 17, and the drawstring 13 is then pulled from outside the body to cinch closed the open end 18 of the pouch 14. When the drawstring 13 is pulled, knot 15 abuts the rod 11 at aperture 12 and, since knot 15 is too large to pass through, it is stopped from moving further. Continued pulling of drawstring 13 results in closing of the noose 15a and, therefore, closing of the mouth 18 of the pouch. The tissue specimen is thereby trapped within the pouch 14. Rod 11 is then pulled proximally out of the cannula, drawing the pouch 14 and excised body tissue therethrough or through the incision in the wall of the body tissue.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. An apparatus for removing body tissue from an interior portion of a body in a minimally invasive surgical procedures, which comprises:
    a) an endoscopic portion configured and dimensioned to be at least partially insertable through a cannula, and having a distal end and a proximal end;
    b) a pouch removably attached to the distal end of said endoscopic portion, said pouch having a first end which is movable between an open configuration and a closed configuration, and a closed second end;
    c) detaching means operatively associated with said pouch for detaching said pouch from said endoscopic portion; and
    d) gaseous seal means disposed in said endoscopic portion for preventing passage of fluid through said endoscopic portion.

2. The apparatus of claim 1 further including closing means operatively associated with said pouch, for moving said first end of said pouch from said open configuration to said closed configuration.

3. The apparatus of claim 2, wherein said detaching means comprises a line of perforations extending circumferentially around said pouch adjacent said first end.

4. The apparatus of claim 3, wherein said pouch includes an upper circumferential sleeve for receiving a pouch support ring.

5. The apparatus of claim 4, wherein said pouch includes a lower circumferential sleeve for receiving said closing means.

6. The apparatus of claim 5, wherein said line of perforations is disposed between said upper circumferential sleeve and said lower circumferential sleeve.

7. The apparatus of claim 2, wherein said closing means comprises a drawstring.

8. The apparatus of claim 7, wherein said gaseous seal means comprises a coating of viscous sealing fluid applied to an outer surface of said drawstring.

9. The apparatus of claim 7, wherein said drawstring forms a running noose disposed circumferentially around said pouch adjacent said first end thereof.

10. The apparatus of claim 9 further including attachment means for attaching a first end portion of said drawstring to a second end portion of said drawstring.

11. The apparatus of claim 10, wherein said attachment means comprises a running knot.

12. The apparatus of claim 10 further including stop means having an aperture for permitting passage therethrough of a single thread line, said second end portion of said drawstring thread extending through said aperture, and said aperture possessing a surface for abutting and holding said attachment means.

13. The apparatus of claim 12, wherein said endoscopic portion comprises a tubular member having a longitudinally extending bore, and a drive rod slidably disposed within said bore for distally moving said pouch from a first position within said tubular member to a second position outside said tubular member, and said stop means comprises a distal surface of said drive rod.

14. The apparatus of claim 13, wherein said aperture is oriented parallel to the longitudinal axis of the drive rod.

15. The apparatus of claim 13 further comprising grasping means located at a proximal end of said drive rod to permit actuation of said drive rod by a single finger of a user's hand.

16. The apparatus of claim 15, wherein said grasping means comprises a drive rod pull ring.

17. The apparatus of claim 16 further including a drawstring pull ring attached to a proximal end of said drawstring.

18. The apparatus of claim 17, wherein said drive rod pull ring includes a reception fixture disposed on a proximal edge thereof, and said drawstring pull ring is removably mounted to said reception fixture.

19. The apparatus of claim 18 further including a knife mounted within said reception fixture.

20. The apparatus of claim 1, wherein said endoscopic portion comprises a tubular member having a longitudinally extending bore, and a drive member slidably disposed within said bore for distally moving said pouch from a first position within said tubular member to a second position outside said tubular member.

21. The apparatus of claim 20, wherein said pouch is removably attached to said drive member.

22. The apparatus of claim 20, wherein said drive member is a cylindrical rod.

23. The apparatus of claim 20 wherein said gaseous seal means comprises a coating of viscous sealing fluid applied to an outer surface of said drive member.

24. The apparatus of claim 1, wherein said detaching means comprises at least one perforation formed in said pouch.

25. The apparatus of claim 1, wherein said pouch is fabricated from a material selected from the group consisting of polyurethane and latex.

26. The apparatus of claim 1, wherein said pouch is fabricated from transparent material which is substantially impervious to passage therethrough of cancer cells.

27. The apparatus of claim 1 further including a knife positioned adjacent the proximal end of said endoscopic portion.

28. An apparatus for removing body tissue from an interior of a body in a minimally invasive surgical procedure, which comprises:
   a) an endoscopic portion configured and dimensioned to be at least partially insertable through a cannula, and having a distal end and a proximal end;
   b) a pouch removably attached to the distal end of said endoscopic portion, said pouch having a first end which is movable between an open configuration and a closed configuration, and a closed second end;
   c) means operatively associated with said pouch for simultaneously moving said first end of said pouch from said open configuration to said closed configuration and detaching said pouch from said endoscopic portion; and
   d) gaseous seal means positioned in said endoscopic portion for preventing passage of fluid through said endoscopic portion.

29. The apparatus of claim 28 further including biasing means operatively communicating with said pouch for resiliently biasing said first end of said pouch to said open configuration.

30. An apparatus for removing body tissue from an interior portion of a body in a minimally invasive surgical procedure, which comprises:
   a) an endoscopic portion configured and dimensioned to be at least partially insertable through a cannula;
   b) a pouch assembly movable between a proximal position at least partially within said endoscopic portion and a distal position at least partially exterior to said endoscopic portion, said pouch assembly including a pouch and a support;
   c) separating means operatively associated with said pouch for separating said pouch from said support; and
   d) gaseous seal means positioned in said endoscopic portion for preventing passage of fluid through said endoscopic portion.

31. The apparatus of claim 30, wherein said separating means includes at least one perforation formed in said pouch.

32. The apparatus of claim 30, wherein said endoscopic portion comprises a tubular member having a longitudinally extending bore, and a drive member slidably disposed within said bore for distally moving said pouch from a first position within said tubular member to a second position outside said tubular member.

33. The apparatus of claim 32, wherein said pouch is removably attached to said drive member.

34. The apparatus of claim 33, wherein said drive member is a cylindrical rod.

35. The apparatus of claim 30, wherein said pouch has a mouth portion which is movable between an open configuration and a closed configuration.

36. The apparatus of claim 35, wherein said separating means comprises a line of perforations extending circumferentially around said pouch adjacent said mouth portion.

37. The apparatus of claim 35 further including closing means, operatively associated with said pouch, for moving said mouth portion of said pouch from said open configuration to said closed configuration.

38. The apparatus of claim 37, wherein said closing means includes a thread.

39. The apparatus of claim 38, wherein said thread forms a running noose disposed circumferentially around said mouth portion.

40. The apparatus of claim 39 further including attachment means for slidably attaching a first end portion of said thread to a second end portion of said thread.

41. The apparatus of claim 40, wherein said attachment means comprises a running knot.

42. The apparatus of claim 40 further including stop means having an aperture for permitting passage therethrough of a single thread line, said second end portion of said thread extending through said aperture, and said aperture possessing a surface for abutting and holding said attachment means.

43. The apparatus of claim 42, wherein said gaseous seal means comprises a coating of viscous sealing fluid applied to an outer surface of said thread.

44. The apparatus of claim 42, wherein said endoscopic portion comprises a tubular member having a longitudinally extending bore, and a drive rod slidably disposed within said bore for distally moving said pouch from a first position within said tubular member to a second position outside said tubular member, and said stop means comprises a distal surface of said drive rod.

45. The apparatus of claim 44, wherein said gaseous sealing means comprises a coating of viscous sealing fluid applied to an outer surface of said drive rod.

46. A surgical apparatus for removing body tissue, which comprises:
   a pouch assembly including a pouch support, and a pouch connected to said pouch support, said pouch having a mouth movable between an open position and a closed position; and
   closing means connected to said pouch for closing said pouch wherein actuation of said closing means also causes separation of said pouch from said pouch support.

47. The surgical apparatus of claim 46, further including an elongated tubular member, said pouch assembly being connected to a distal end of said elongated tubular member.

48. The surgical apparatus of claim 46, wherein said closing means comprises a thread disposed circumferentially around the mouth of said pouch.

49. The surgical apparatus of claim 46, wherein said pouch includes a linear weakened portion extending circumferentially around the mouth of the pouch to facilitate separation of said pouch from said pouch support.

50. The surgical apparatus of claim 46, wherein said pouch is fabricated from a material selected from the group consisting of polyurethane and latex.

51. The surgical apparatus of claim 46, wherein the pouch is fabricated from a transparent material.

52. An apparatus for removing body tissue from an interior portion of a body in a minimally invasive surgical procedure, which comprises:
 a) an endoscopic portion configured and dimensioned to be at least partially insertable through a cannula;
 b) a pouch assembly movable between a proximal location within said endoscopic portion and a distal location exterior to said endoscopic portion, said pouch having a first end which is movable between an open configuration and a closed configuration, and a closed second end;
 c) a thread operatively associated with said pouch, for closing said first end of said pouch; and
 d) cutting means located proximally of said pouch assembly for cutting said thread.

53. The apparatus of claim 52 further including gaseous seal means positioned in said endoscopic portion for preventing passage of fluid through said endoscopic portion.

54. The apparatus of claim 52, wherein said pouch assembly includes a pouch support and a pouch connected to said pouch support, and separating means for separating said pouch from said pouch support.

55. The apparatus of claim 54, wherein said separating means includes at least one perforation formed in said pouch.

56. The apparatus of claim 54, wherein said separating means comprises a line of perforations extending circumferentially around said pouch adjacent said first end of said pouch.

57. The apparatus of claim 52, wherein said endoscopic portion comprises a tubular member having a longitudinally extending bore, and a drive member slidably disposed within said bore for distally moving said pouch from a first position within said tubular member to a second position outside said tubular member.

58. The apparatus of claim 57, wherein said pouch is removably attached to said drive member.

59. The apparatus of claim 58, wherein said drive member is a cylindrical rod.

60. The apparatus of claim 52, wherein said thread forms a running noose disposed circumferentially around said first end of said pouch.

61. The apparatus of claim 60 further including attachment means for slidably attaching a first end portion of said thread to a second end portion of said said.

62. The apparatus of claim 61, wherein said attachment means comprises a running knot.

63. The apparatus of claim 61 further including stop means having an aperture for permitting passage therethrough of a single thread line, said second end portion of said thread extending through said aperture, and said aperture possessing a surface for abutting and holding said attachment means.

64. The apparatus of claim 63, wherein said endoscopic portion comprises a tubular member having a longitudinally extending bore, and a drive rod slidably disposed within said bore for distally moving said pouch from a first position within said tubular member to a second position outside said tubular member, and said stop means comprises a distal surface of said drive rod.

65. The apparatus of claim 64 further including gaseous sealing means positioned in said endoscopic portion for preventing passage of fluid through said endoscopic portion.

66. The apparatus of claim 65, wherein said gaseous sealing means comprises a coating of viscous sealing fluid applied to an outer surface of said drive rod.

67. The apparatus of claim 65, wherein said gaseous sealing means comprises a coating of viscous sealing fluid applied to an outer surface of said thread.

68. An apparatus for removing body tissue from an interior portion of a body in a minimally invasive surgical procedure, which comprises:
 a) an endoscopic portion configured and dimensioned to be at least partially insertable through a cannula, and having a distal end and a proximal end;
 b) a pouch removably attached to the distal end of said endoscopic portion, said pouch having a first end which is movable between an open configuration and a closed configuration, and a closed second end;
 c) detaching means operatively associated with the first end of said pouch for detaching said pouch from said endoscopic portion, said detaching means comprising at least one perforation formed in said pouch.

69. An apparatus for removing body tissue from an interior portion of a body in a minimally invasive surgical procedure, which comprises:
 a) an endoscopic portion configured and dimensioned to be at least partially insertable through a cannula, and having a distal end and a proximal end;
 b) a pouch removably attached to the distal end of said endoscopic portion, said pouch having a first end which is movable between an open configuration and a closed configuration, and a closed second end;
 c) detaching means operatively associated with said pouch for detaching said pouch from said endoscopic portion; and
 d) a knife located proximally to said endoscopic portion.

* * * * *